US010363372B2

(12) United States Patent
Nazzaro

(10) Patent No.: US 10,363,372 B2
(45) Date of Patent: Jul. 30, 2019

(54) PLUNGER FOR DRUG DELIVERY DEVICE

(71) Applicant: Insulet Corporation, Acton, MA (US)

(72) Inventor: David Nazzaro, Groveland, MA (US)

(73) Assignee: INSULET CORPORATION, Acton, MA (US)

( * ) Notice: Subject to any disclaimer, the term of this patent is extended or adjusted under 35 U.S.C. 154(b) by 0 days.

(21) Appl. No.: 15/674,974

(22) Filed: Aug. 11, 2017

(65) Prior Publication Data

US 2018/0043106 A1 Feb. 15, 2018

Related U.S. Application Data

(60) Provisional application No. 62/449,845, filed on Jan. 24, 2017, provisional application No. 62/449,849, (Continued)

(51) Int. Cl.
*A61M 5/315* (2006.01)
*A61M 5/24* (2006.01)
(Continued)

(52) U.S. Cl.
CPC ...... *A61M 5/31578* (2013.01); *A61M 5/2429* (2013.01); *A61M 5/283* (2013.01); (Continued)

(58) Field of Classification Search
CPC ...... A51M 5/145; A51M 5/315; A51M 5/283; A51M 5/2429; A51M 5/31513; (Continued)

(56) References Cited

U.S. PATENT DOCUMENTS 1,441,508 A 1/1923 Marius et al.
3,885,662 A 5/1975 Schaefer
(Continued)

FOREIGN PATENT DOCUMENTS

CA 606281 A 10/1960
DE 4200595 A1 7/1993
(Continued)

OTHER PUBLICATIONS

Lind, et al.,"Linear Motion Miniature Actuators." Paper presented at the 2nd Tampere International Conference on Machine Automation, Tampere, Finland (Sep. 1998), 2 pages.
(Continued)

*Primary Examiner* — Imani N Hayman
*Assistant Examiner* — Tiffany Legette

(57) ABSTRACT

Plunger systems for expelling a liquid drug from a drug container within a wearable drug delivery device are provided. A rotation system coupled to a plunger rotates the plunger about a central axis of the plunger to overcome a static friction between the plunger and the drug container. After rotating the plunger, a drive system moves the plunger forward into the drug container to expel the liquid drug for delivery to the patient. A collapsible plunger includes a cavity. A radial torsion spring positioned in the cavity can provide an outward radial force on the collapsible plunger. The cavity enables the collapsible plunger to compress radially when entering and passing through a region of a drug container having a relatively narrower width. The radial torsion spring can radially expand the collapsible plunger when entering and passing through a region of the drug container having a relatively wider width.

22 Claims, 14 Drawing Sheets

700 904 708 706 806 704 908 724 906 802 702 804 902 722 710 712

Related U.S. Application Data filed on Jan. 24, 2017, provisional application No. 62/385,749, filed on Sep. 9, 2016, provisional application No. 62/375,026, filed on Aug. 15, 2016, provisional application No. 62/374,881, filed on Aug. 14, 2016, provisional application No. 62/374,394, filed on Aug. 12, 2016.

(51) Int. Cl.
*A61M 5/28* (2006.01)
*A61M 5/145* (2006.01)
*A61M 5/31* (2006.01)

(52) U.S. Cl.
CPC .... *A61M 5/31513* (2013.01); *A61M 5/31535* (2013.01); *A61M 5/145* (2013.01); *A61M 2005/3109* (2013.01)

(58) Field of Classification Search
CPC .......... A51M 5/31535; A51M 5/31578; A51M 5/31511; A51M 5/31515; A61M 2005/14506; A61J 1/20; A61J 1/201; A61J 1/2006; A61J 1/2096
See application file for complete search history.

(56) References Cited

U.S. PATENT DOCUMENTS 4,108,177 A 8/1978 Pistor
4,268,150 A 5/1981 Chen
4,313,439 A 2/1982 Babb et al.
4,424,720 A 1/1984 Bucchianeri
4,435,173 A 3/1984 Siposs et al.
4,498,843 A 2/1985 Schneider et al.
4,507,115 A 3/1985 Kambara et al.
4,551,134 A 11/1985 Slavik et al.
4,562,751 A 1/1986 Nason et al.
4,585,439 A 4/1986 Michel
4,601,707 A 7/1986 Albisser et al.
4,634,427 A 1/1987 Hannula et al.
4,678,408 A 7/1987 Nason et al.
4,684,368 A 8/1987 Kenyon
4,755,169 A 7/1988 Sarnoff et al.
4,898,579 A 2/1990 Groshong et al.
4,944,659 A 7/1990 Labbe et al.
4,969,874 A 11/1990 Michel et al.
5,007,458 A 4/1991 Marcus et al.
5,062,841 A 11/1991 Siegel
5,205,819 A 4/1993 Ross et al.
5,213,483 A 5/1993 Flaherty et al.
5,261,882 A 11/1993 Sealfon
5,281,202 A 1/1994 Weber et al.
5,346,476 A 9/1994 Elson
5,364,342 A 11/1994 Beuchat et al.
5,433,710 A 7/1995 VanAntwerp et al.
5,582,593 A 12/1996 Hultman
5,637,095 A 6/1997 Nason et al.
5,665,070 A 9/1997 McPhee
5,713,875 A 2/1998 Tanner, II
5,747,350 A 5/1998 Sattler
5,748,827 A 5/1998 Holl et al.
5,776,103 A 7/1998 Kriesel et al.
5,779,676 A 7/1998 Kriesel et al.
5,785,688 A 7/1998 Joshi et al.
5,797,881 A 8/1998 Gadot
5,800,397 A 9/1998 Wilson et al.
5,807,075 A 9/1998 Jacobsen et al.
5,839,467 A 11/1998 Saaski et al.
5,891,097 A 4/1999 Saito et al.
5,897,530 A 4/1999 Jackson
5,906,597 A 5/1999 McPhee
5,911,716 A 6/1999 Rake et al.
5,919,167 A 7/1999 Mulhauser et al.
5,957,890 A 9/1999 Mann et al.
5,961,492 A 10/1999 Kriesel et al.
6,019,747 A 2/2000 McPhee
6,174,300 B1 1/2001 Kriesel et al.
6,190,359 B1 2/2001 Heruth
6,200,293 B1 3/2001 Kriesel et al.
6,363,609 B1 4/2002 Pickren
6,375,638 B2 4/2002 Nason et al.
6,474,219 B2 11/2002 Klitmose et al.
6,485,461 B1 11/2002 Mason et al.
6,485,462 B1 11/2002 Kriesel
6,488,652 B1 12/2002 Weijand et al.
6,520,936 B1 2/2003 Mann
6,527,744 B1 3/2003 Kriesel et al.
6,537,249 B2 3/2003 Kriesel et al.
6,569,115 B1 5/2003 Barker
6,595,956 B1 7/2003 Gross et al.
6,656,158 B2 12/2003 Mahoney et al.
6,699,218 B2 3/2004 Flaherty et al.
6,723,072 B2 4/2004 Flaherty et al.
6,883,778 B1 4/2005 Newton et al.
7,144,384 B2 12/2006 Gorman et al.
7,160,272 B1 1/2007 Eyal et al.
8,939,935 B2 1/2015 O'Connor et al.
9,180,244 B2 11/2015 Anderson et al.
9,192,716 B2 11/2015 Jugl et al.
9,402,950 B2 8/2016 Dilanni et al.
2001/0056258 A1 12/2001 Evans
2002/0173769 A1 11/2002 Gray et al.
2003/0040715 A1 2/2003 D'Antonio et al.
2004/0064088 A1 4/2004 Gorman et al.
2004/0068224 A1 4/2004 Couvillon, Jr. et al.
2004/0069044 A1 4/2004 Lavi et al.
2005/0020980 A1 1/2005 Inoue et al.
2005/0203461 A1 9/2005 Flaherty et al.
2005/0238507 A1 10/2005 Dilanni et al.
2006/0041229 A1 2/2006 Garibotto et al.
2006/0079765 A1 4/2006 Neer et al.
2006/0178633 A1 8/2006 Garibotto et al.
2008/0114304 A1 5/2008 Nalesso et al.
2008/0172028 A1 7/2008 Blomquist
2010/0036326 A1 2/2010 Matusch
2010/0241066 A1 9/2010 Hansen et al.
2011/0144586 A1 6/2011 Michaud et al.
2013/0245545 A1 9/2013 Arnold et al.
2014/0018730 A1 1/2014 Muller-Pathle
2014/0142508 A1 5/2014 Dilanni et al.
2014/0171901 A1* 6/2014 Langsdorf ............. A61M 5/001 604/506
2015/0041498 A1* 2/2015 Kakiuchi ............. A61M 5/284 604/191
2015/0202386 A1 7/2015 Brady et al.
2017/0021096 A1 1/2017 Cole et al.
2017/0021137 A1 1/2017 Cole
2017/0239415 A1 8/2017 Hwang et al.

FOREIGN PATENT DOCUMENTS

EP 0867196 A2 9/1998
EP 1177802 A1 2/2002
EP 2468338 A1 6/2012
EP 2703024 A1 3/2014
FR 2096275 A5 2/1972
GB 357139 A1 9/1931
GB 810488 A 3/1959
GB 2549750 A 11/2017
IL 46017 A 11/1977
JP H08238324 A 9/1996
WO 8101658 A 6/1981
WO 8606796 A1 11/1986
WO 9855073 A1 12/1998
WO 9910040 A1 3/1999
WO 9910049 A1 3/1999
WO 9962576 A1 12/1999
WO 200178812 A1 10/2001
WO 200226282 A2 4/2002
WO 2002076535 A1 10/2002
WO 2003097133 A1 11/2003
WO 2007066152 A1 6/2007
WO 2009039203 A2 3/2009

(56) References Cited

FOREIGN PATENT DOCUMENTS

| | | | |
|---|---|---|---|
| WO | 2010139793 | A1 | 12/2010 |
| WO | 2011033823 | A1 | 3/2011 |
| WO | 2011075042 | A1 | 6/2011 |
| WO | 2012073032 | A1 | 6/2012 |
| WO | 2013050535 | A2 | 4/2013 |
| WO | 2014149357 | A1 | 9/2014 |
| WO | 2015081337 | A2 | 6/2015 |
| WO | 2015117854 | A1 | 8/2015 |
| WO | 2015167201 | A1 | 11/2015 |
| WO | 2015177082 | A1 | 11/2015 |
| WO | 2017187177 | A1 | 11/2017 |

OTHER PUBLICATIONS

Author unknown, "The Animas R-1000 Insulin Pump—Animas Corporation intends to exit the insulin pump business and discontinue the manufacturing and sale of Animas® Vibe® and OneTouch Ping® insulin pumps." [online], Dec. 1999 [retrieved on Oct. 16, 2018]. Retrieved from the Internet URL: http://www.animaspatientsupport.com/.

Author unknown, CeramTec "Discover the Electro Ceramic Products CeramTec acquired from Morgan Advanced Materials" [online], Mar. 1, 2001 [retrieved on Oct. 17, 2018]. Retrieved from the Internet URL: http://www.morgantechnicalceramics.com/, 2 pages.

Vaughan, M.E., "The Design, Fabrication, and Modeling of a Piezoelectric Linear Motor." Master's thesis, Virginia Polytechnic Institute and State University, VA. (2001).

Galante, et al., "Design, Modeling, and Performance of a High Force Piezoelectric Inchworm Motor," Journal of Intelligent Material Systems and Structures, vol. 10, 962-972 (1999).

International Search Report and Written Opinion for application No. PCT/US2017/034811, dated Oct. 18, 2017, 15 pages.

International Search Report and Written Opinion for application No. PCT/US17/46508 dated Jan. 17, 2018, 14 pages.

International Search Report and Written Opinion for application No. PCT/US17/46777, dated Dec. 13, 2017 14 pages.

International Search Report and Written Opinion for application No. PCT/US17/46737, dated Dec. 14, 2017 11 pages.

International Search Report and Written Opinion for application No. PCT/US17/55054, dated Jan. 25, 2018 13 pages.

International Search Report and Written Opinion for PCT/US2018/014351, dated Jun. 4, 2018, 11 pages.

International Search Report and Written Opinion for application No. PCT/US18/45155, dated Oct. 15, 2018, 15 pages.

International Search Report and Written Opinion for application No. PCT/US2017/34814, dated Oct. 11, 2017, 16 pages.

* cited by examiner

PLUNGER FOR DRUG DELIVERY DEVICE

CROSS-REFERENCE TO RELATED APPLICATIONS

This application claims the benefit of U.S. Provisional Application No. 62/374,394, filed Aug. 12, 2016, U.S. Provisional Application No. 62/374,881, filed Aug. 14, 2016, U.S. Provisional Application No. 62/375,026, filed Aug. 15, 2016, U.S. Provisional Application No. 62/385,749, filed Sep. 9, 2016, U.S. Provisional Application No. 62/449,845, filed Jan. 24, 2017, and U.S. Provisional Application No. 62/449,849, filed Jan. 24, 2017, each of which is incorporated herein by reference in its entirety.

TECHNICAL FIELD

Embodiments generally relate to medication delivery. More particularly, embodiments relate to plungers for expelling liquids from drug containers.

BACKGROUND

Many conventional drug delivery systems include a drug container that stores a liquid drug. The liquid drug is expelled from the drug container for delivery to a patient. Many standardized drug containers have multiple internal regions of different diameters, thereby preventing the use of a plunger to expel the stored liquid drug. As a result, complex and bulky pump systems are often used to extract the liquid drug from such drug containers. Other drug containers are specifically designed to accommodate the use of a plunger. However, when the plunger is moved forward into such a drug container from an initial resting position to expel the liquid drug, a surge of liquid drug can be provided to the patient, resulting in patient discomfort. A need therefore exists for systems that can efficiently expel a liquid drug from various different types of drug containers while minimizing any discomfort to the user and reducing cost and space requirements.

DETAILED DESCRIPTION

Figure 1:
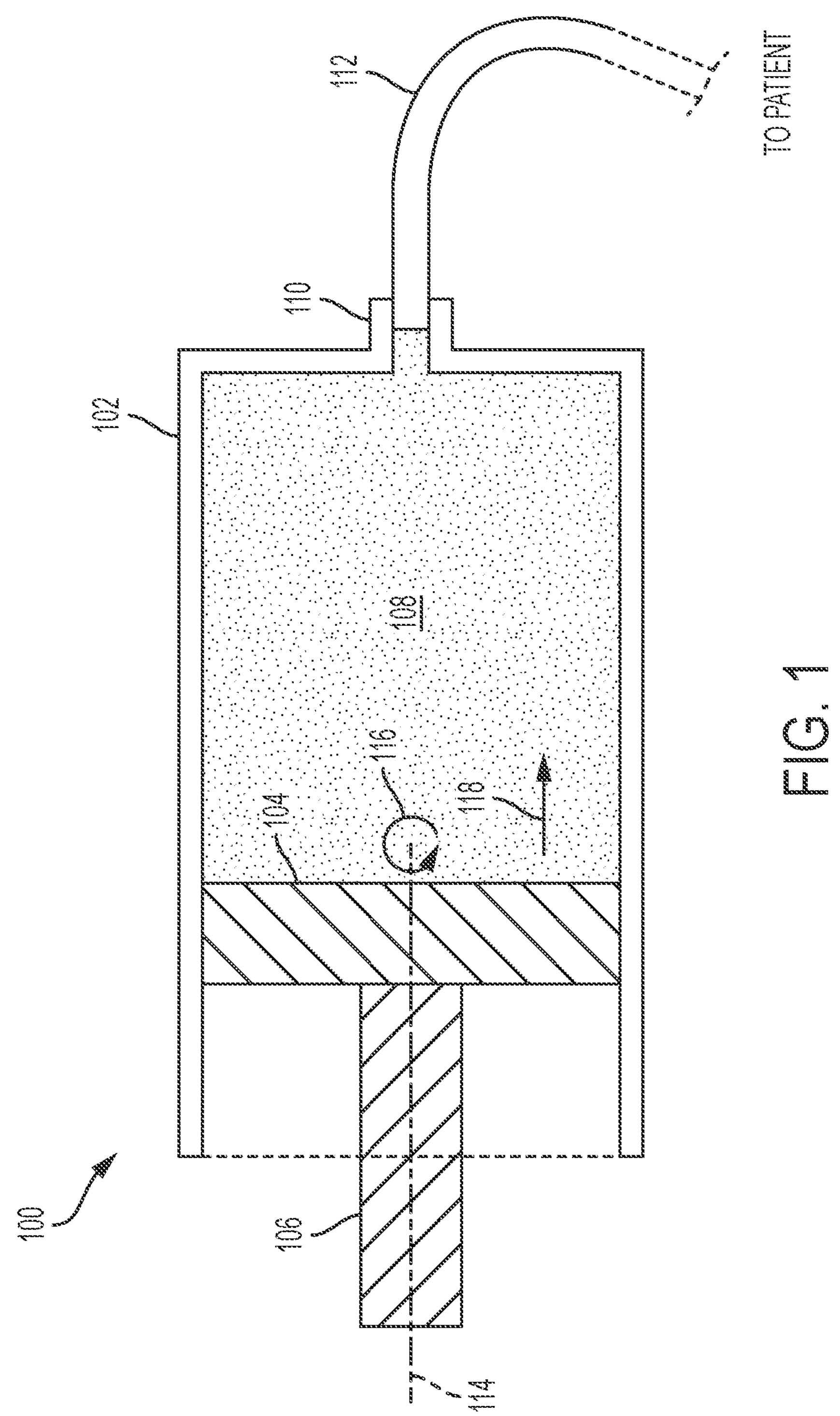
FIG. 1 illustrates a first exemplary embodiment of a plunger system.

This disclosure presents various systems, components, and methods for expelling a liquid drug from a drug container. Each of the systems, components, and methods disclosed herein provides one or more advantages over conventional systems, components, and methods.

Various embodiments include plunger systems for expelling a liquid drug from a drug container within a wearable drug delivery device. In various embodiments, a rotation system is coupled to a plunger. The rotation system rotates the plunger about a central axis of the plunger to overcome a static friction between the plunger and the drug container. After rotating the plunger, a drive system moves the plunger forward into the drug container to expel the liquid drug for delivery to the patient. Rotating the plunger to overcome the static friction reduces any surge effect of the liquid drug during initial drug delivery, thereby improving patient comfort.

In various embodiments, a collapsible plunger is provided to expel a liquid drug from a container having regions of different sizes. The collapsible plunger includes a central cavity. A radial torsion spring positioned in the cavity can provide an outward radial force on the collapsible plunger. The cavity enables the collapsible plunger to compress radially when entering and passing through a region of a drug container having a relatively narrower width. The radial torsion spring can radially expand the collapsible plunger when entering and passing through a region of the drug container having a relatively wider width. Accordingly, the width of the collapsible plunger can adjust to and match the variable width of the drug container. Other embodiments are disclosed and described.

For many drug delivery systems, a drug container is used to hold or store a liquid drug prior to delivering the liquid drug to a patient. A plunger is often used to expel the liquid drug from the drug container. In general, as the plunger is advanced into the drug container, a corresponding amount of the liquid drug is expelled from the drug container that can then be provided to a patient. A drive system is often used to provide a force that moves the plunger in a desired direction to expel the liquid drug from the drug container.

Generally, the drug container can be cylindrical in shape and/or have a circular cross-sectional shape. An outer cylindrical surface of the plunger forms a seal with the internal surface and/or walls of the drug container to retain the liquid drug within the drug container. To advance the plunger from an initial resting position, a force must be provided that overcomes static friction caused by the interaction of the sealing surfaces of the plunger and the drug container. The force for overcoming this static friction is often referred to as a break force. After overcoming the static friction, a force must subsequently be provided to continue advancement of the plunger. The force for continuing advancement of the plunger after overcoming the static friction is often referred to as a running force.

For many drug delivery systems, the amount of force required to overcome the static friction (e.g., the break force) can be significantly larger than the amount of force required to continue advancement of the plunger (e.g., the running force). In many instances, the break force can be at least twice as large as the running force. Accordingly, drive systems designed for controlling the movement of a plunger must be able to provide a break force that is at least twice as large as the running force. Typically, for safety reasons and other operational concerns, these drive systems are designed to continuously provide relatively higher break force levels when controlling movement of a plunger as opposed to relatively lower running force levels. As a result, these drive systems can be more costly and can occupy more space than drive systems that are not required to continuously provide relatively higher break force levels.

Additionally, the patient may experience pain or other discomfort when a break force is applied to overcome the static friction between the plunger and the drug container. For example, a momentary surge of liquid drug may result when the static friction is overcome by a drive system applying a break force, which can make an initial infusion of the liquid drug uncomfortable for the patient.

Accordingly, there is a need for a plunger system for expelling a liquid drug from a drug container that can overcome the static friction related to operation of the plunger while also minimizing any discomfort experienced by the patient and that is less costly and occupies less space than conventional plunger systems.

FIG. 1 illustrates a plunger system 100 for providing improved plunger operation. In particular, the plunger system 100 can reduce a break force required to be applied to a plunger before it can be caused to advance in a direction to expel a liquid drug from a drug container. As a result, a lower cost and smaller sized drive system for controlling movement of the plunger can be used with the plunger system 100. Further, comfort of the patient, particularly during initial movement of the plunger, can be improved.

As shown in FIG. 1, the plunger system 100 can include a drug container 102, a plunger 104, and a push rod 106. The drug container 102 can be any type of drug container including, for example, a vial, a syringe, or a cartridge. In general, the drug container 102 can be any type of drug container for holding a liquid drug that has a circular cross-section. FIG. 1 illustrates the plunger system 100 in cross-section.

The drug container 102 can hold a liquid drug 108. The plunger 104 can be coupled to the push rod 106. The push rod 106 can be coupled to any portion of the plunger 104. The push rod 106 can apply a force to the plunger 104 to advance the plunger 104 into the drug container 102. As a result, the liquid drug 108 can be expelled through a port 110 of the drug container 102. The port 110 can be coupled to a needle, a needle conduit, and/or tubing 112 that can deliver the expelled liquid drug 108 to a patient.

The plunger system 100 can be used with or can be part of any drug delivery system such as, for example, a pin injector or a wearable drug delivery device. Further, the plunger system 100 can be used to deliver any liquid drug 108 to a user including, for example, any drug, medicine, biologic, or therapeutic agent. The plunger 104 can comprise a plastic, rubber, and/or an elastomer material. The drug container102 can comprise a plastic and/or a glass material.

The plunger system 100 can provide break force mitigation by rotating the plunger 104 about a central axis 114 of the plunger 104 prior to advancing the plunger 104 into the drug container 102. Specifically, the plunger 104 and/or push rod 106 can be coupled to a drive system that can rotate the plunger 104 in a clockwise or a counterclockwise direction to overcome the static friction prior to pushing the plunger 104 into the drug container 102 towards the port 110. The central axis 114 can be a longitudinal axis of the plunger 104 relative to the depiction of the plunger system 100 in FIG. 1.

As the break force required to rotate the plunger 104 about the central axis 114 is less than the break force required to move the plunger 104 forward further into the drug container 102, less force can be applied to overcome the static friction. After the static friction is overcome, the drive system can then apply a force on the push rod 106 along the direction of the central axis 114 (or substantially parallel thereto) to move the plunger 104 forward to expel the liquid drug 108 from the drug container 102. Indicator 116 illustrates an exemplary direction of rotation of the plunger 104 relative to the central axis 114 of the plunger 104. Indicator 118 illustrates a direction of movement of the plunger 104 after the plunger 104 has been rotated to overcome the static friction between the plunger 104 and the drug container 102.

In various embodiments, a first drive system can be used to rotate the plunger 104 (e.g., as shown by direction indicator 116) and a second drive system can be used to move the plunger 104 forward (e.g., as shown by direction indicator 118). Alternatively, in various embodiments, the same drive system can be used to apply the break force and the running force. The plunger system 100 can be used for a single dose drug delivery system or a multiple dose drug delivery system in which the plunger 104 is stopped and advanced multiple times.

Figure 2:
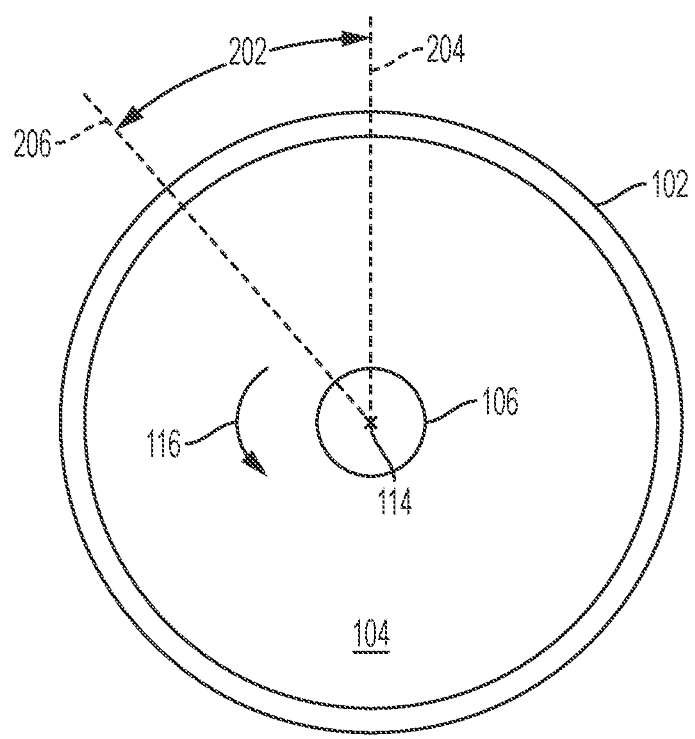
FIG. 2 illustrates a second view of the plunger system of FIG. 1.

FIG. 2 shows a second view of the plunger system 100 of FIG. 1. Specifically, FIG. 2 shows a view of the plunger system 100 from behind the plunger 104 and facing the drug container 102. As shown in FIG. 2, the drug container 102 can have a circular cross-section. As further shown in FIG. 2, the plunger 104 can be rotated by an amount 202 from an initial position 204 to a final position 206 relative to the direction indicator 116. The rotation amount 202 can be any amount and can be in a clockwise and/or a counterclockwise direction (e.g., relative to the view of the plunger system 100 depicted in FIG. 1). The rotation amount 202 can be such that the static friction between the plunger 104 and the drug container 102 is overcome. Once the static friction is overcome, the push rod 106 can be used to advance the plunger 104 forward (e.g., into the drug container 102). In various embodiments, the rotation amount 202 can be less than 45 degrees. In various embodiments, the rotation amount 202 can be a few degrees such as, for example, less than 10 or 5 degrees.

Figure 3:
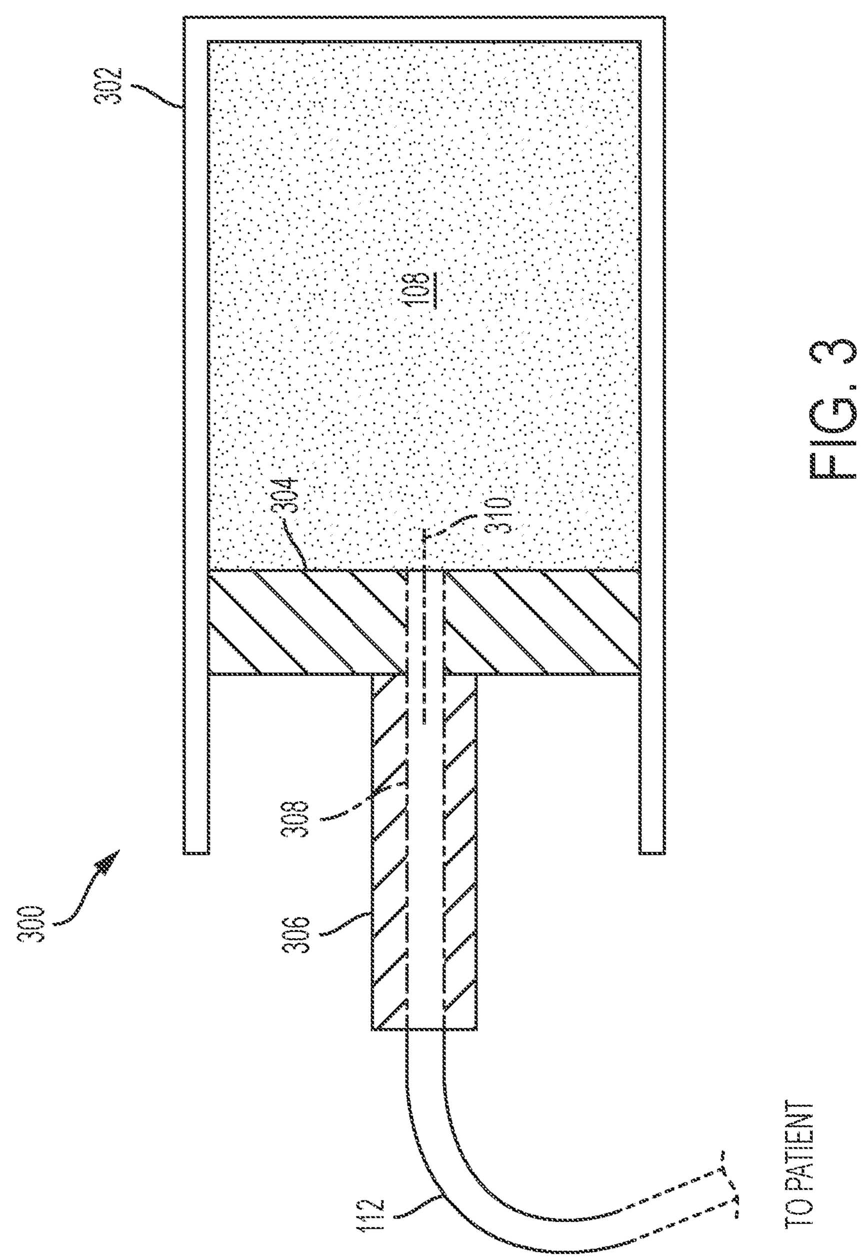
FIG. 3 illustrates a second exemplary embodiment of a plunger system.

FIG. 3 illustrates a second plunger system 300 for providing improved plunger operation. As with the plunger system 100, the plunger system 300 can be used to mitigate a required break force. The plunger system 300 can operate in a substantially similar manner as the plunger system 100 to provide break force mitigation. As shown in FIG. 3, the plunger system 300 can include a drug container 302, a plunger 304, and a push rod 306. The drug container 302 can be substantially equivalent to the drug container 102. The plunger 304 and the push rod 306 can each be substantially equivalent to the plunger 104 and the push rod 106, respectively. FIG. 3 illustrates the plunger system 300 in cross-section.

Instead of the drug container 302 having a port at an end for the liquid drug 108 to be expelled, the plunger 304 and the push rod 306 can provide an internal port or fluid path 308. The port 308 can enable the liquid drug 108 to be expelled from the drug container 302 through the plunger 304 and the push rod 306 and on to the needle, needle conduit, or tubing 112. In this way, as the plunger 304 is advanced into the drug container 302, the liquid drug 108 can be expelled out through an opposite end of the drug container 302 in comparison to the arrangement of the plunger system 100. The needle 112 can be positioned within any portion of the port 308, can be positioned adjacent to an end of the push rod 306, or can form a portion of the port 308.

As explained in relation to the plunger system 100, the plunger system 300 can also provide break force mitigation by enabling rotation of the plunger 304 about a central axis 310 of the plunger 308 as discussed above in relation to FIGS. 1 and 2. In particular, the plunger 308 can be rotated about the central axis 310 to overcome a static friction between the plunger 308 and the drug container 302. Subsequently, the plunger 308 can be advanced to expel the liquid drug 108 from the drug container 302.

In various embodiments described herein, the push rod can be connected or coupled to the plunger to enable a rotation of the push rod to result in rotation of the plunger. For example, the plunger and push rod can be coupled together by a keyed feature that allows the push rod and plunger to rotate together when the push rod is rotated. Such coupling features can be implemented with the plungers 104 and 304 and corresponding push rods 106 and 306 described herein.

Figure 4:
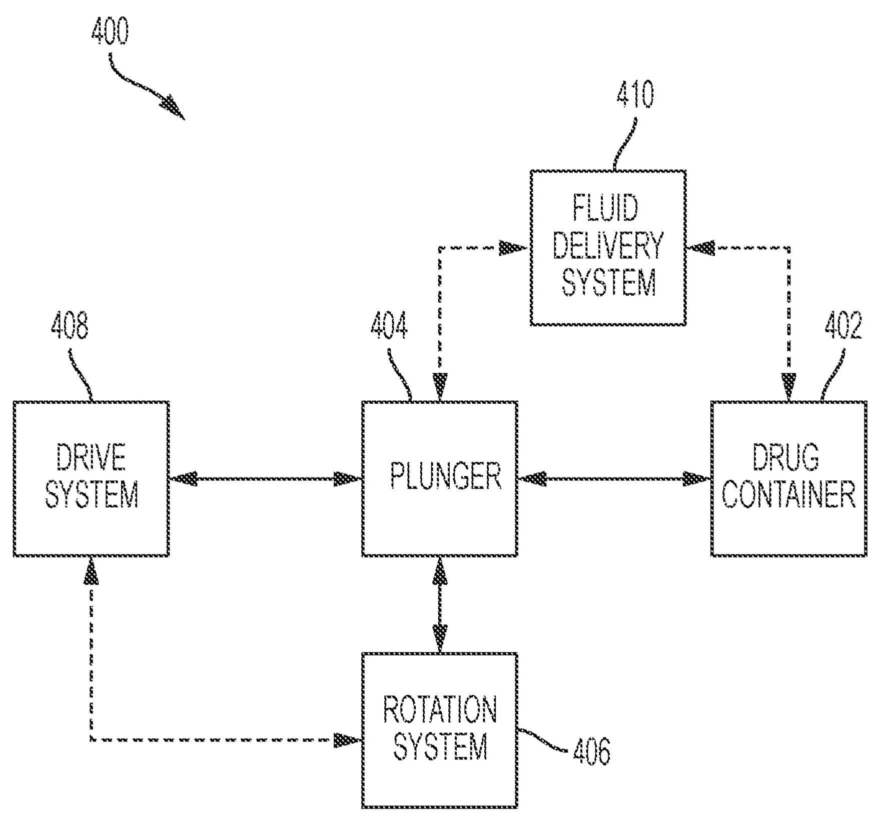
FIG. 4 illustrates a block diagram of a third exemplary embodiment of a plunger system.

FIG. 4 illustrates a block diagram of various components of a plunger system 400 providing break force mitigation. The plunger system 400 can represent the plunger system 100 and/or the plunger system 300. The plunger system 400 includes a drug container 402. The drug container 402 can represent the drug container 102 or the drug container 302. The plunger system 400 further includes a plunger 404. The plunger 404 can represent the plunger 104 or the plunger 304.

The plunger system 400 further includes a rotation system 406. The rotation system 406 can provide the ability to rotate the plunger 404 about a central axis of the plunger 404 (e.g., in a clockwise and/or a counterclockwise direction). The rotation system 406 can rotate the plunger 404 by an amount and with a force to overcome static friction between the plunger 404 and any interior portion or walls of the drug container 402.

The plunger system 400 can also include a drive system 408. The drive system 408 can provide the ability to move the plunger 404 in a forward or backwards direction relative to the drug container 402. That is, the drive system 408 can advance the plunger 404 into the drug container 402 to expel liquid drug from the drug container 402. In various embodiments, the drive system 408 can include the rotation system 406. That is, the drive system 408 and the rotation system 406 can be a combined system or component (as indicated by the dotted line linking the drive system 408 and the rotation system 406). In various embodiments, the drive system 408 and the rotation system 406 can be separate and/or distinct systems. In various embodiments, the drive system 408 can include the push rod 106 and/or the push rod 306. In various embodiments, the push rod 106 and/or the push rod 306 can be considered to be part of the plunger 404. In various embodiments, the drive system 408 can apply a force to the plunger 402 to move the plunger 402 using one or more mechanisms other than a push rod such as, for example, a linear drive spring.

A fluid delivery system 410 can be coupled to the plunger 404 or the drug container 402. The fluid delivery system 410 can include a needle, a needle conduit, and/or tubing that can be used as a fluid path for delivering expelled liquid drug from the drug container 402 to a patient. When the fluid delivery system 410 is coupled to the drug container 402, the plunger system 400 can represent the plunger system 100. When the fluid delivery system 410 is coupled to the plunger 404, the plunger system 400 can represent the plunger system 300.

A variety of mechanisms can be used for the rotation system 406 so as to provide the ability to rotate the plunger 404 by a desired amount in either a clockwise or counterclockwise direction using a desired amount of force. In various embodiments, the rotation system 406 can be an entirely mechanical system. In various other embodiments, the rotation system 406 can be an electromechanical system.

As an example, the rotation system 406 can include a torsion spring coupled to the plunger 404 (and/or coupled to a push rod that is coupled to the plunger 404). The torsion spring can be activated (e.g., released) from an initial position to cause the plunger 404 to rotate. As another example, the rotation system 406 can be part of the drive system 408 that can initially rotate the plunger 404 (e.g., by rotating a push rod coupled to the plunger 404) and then subsequently translate the plunger 404 forward (e.g., by pushing on a push rod coupled to the plunger 404).

Figure 5:
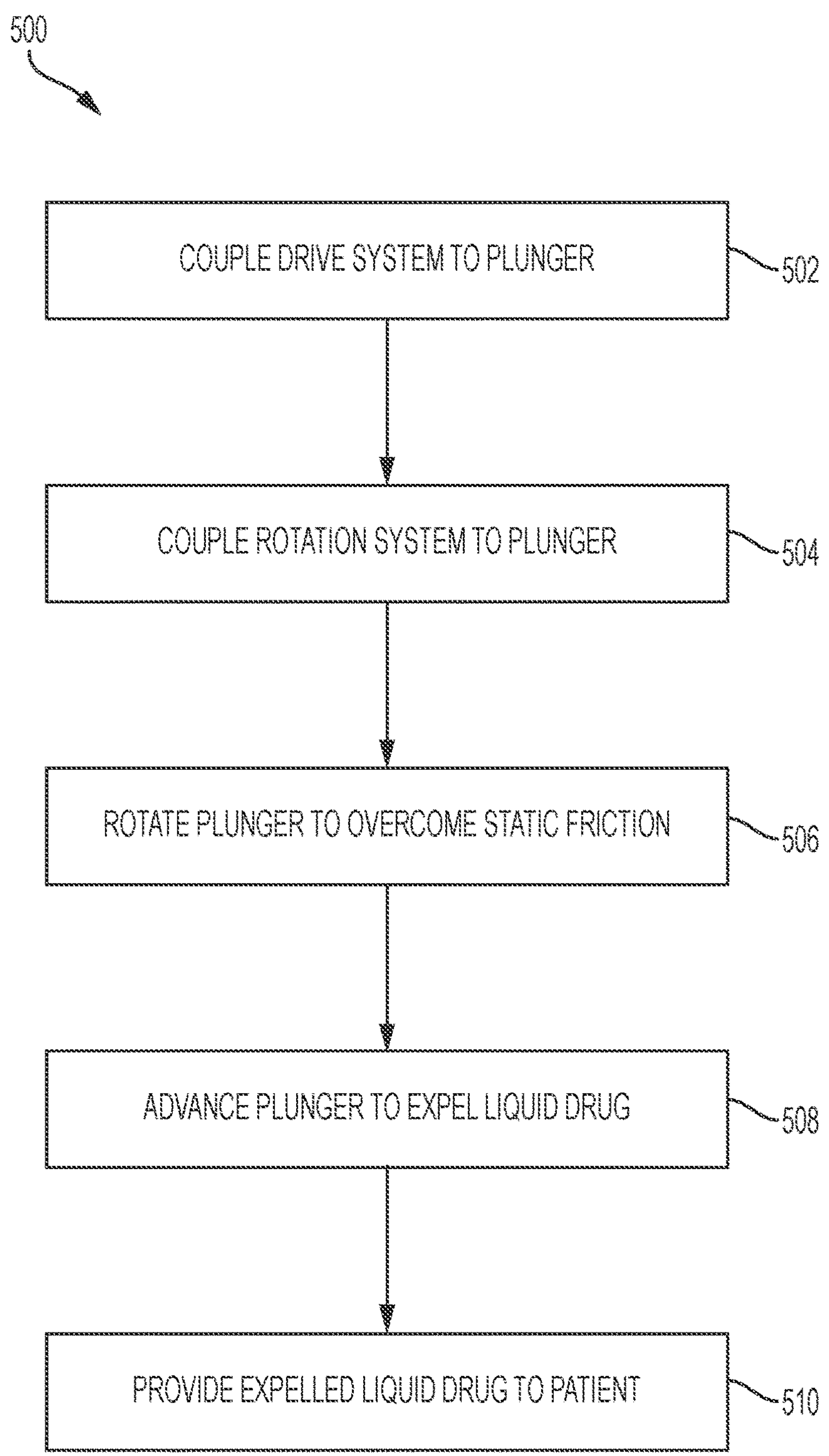
FIG. 5 illustrates an exemplary method of operation for the plunger systems of FIGS. 1-4.

FIG. 5 illustrates an exemplary method of operation 500 for a plunger system providing break force mitigation. The method of operation 500 can be implemented by the plunger system 100, the plunger system 300, and/or the plunger system 400.

At 502, a drive system can be coupled to a plunger of a plunger system. At 504, a rotation system can be coupled to the plunger. At 506, the plunger can be rotated by a predetermined amount using a predetermined force to overcome static friction between the plunger and a drug container holding a liquid drug. The plunger can be rotated by the rotation system. The plunger can be rotated about a central axis in a clockwise and/or a counterclockwise direction. A break force can be considered to be applied at 506.

At 508, after the static friction has been overcome, the plunger can be advanced into the drug container (e.g., further into or further inside of the drug container). The drive system can provide a force to move the plunger in a direction to expel the liquid drug from the drug container. A running force can be considered to be applied at 508.

At 510, the expelled drug can be provided to a patient. The drug can be provided to the patient using a fluid delivery system that can include, for example, a needle, a needle conduit, and/or tubing. The liquid drug can be expelled through a port of the drug container or through a port of the plunger.

Any portion of the method of operation 500 can be repeated. For example, for a plunger system providing multiple doses of a liquid drug to a patient over time, 506-510 can be repeated to sequentially and repeatedly provide a break force and then a running force to enable the plunger to expel the liquid drug from the drug container.

Figure 6:
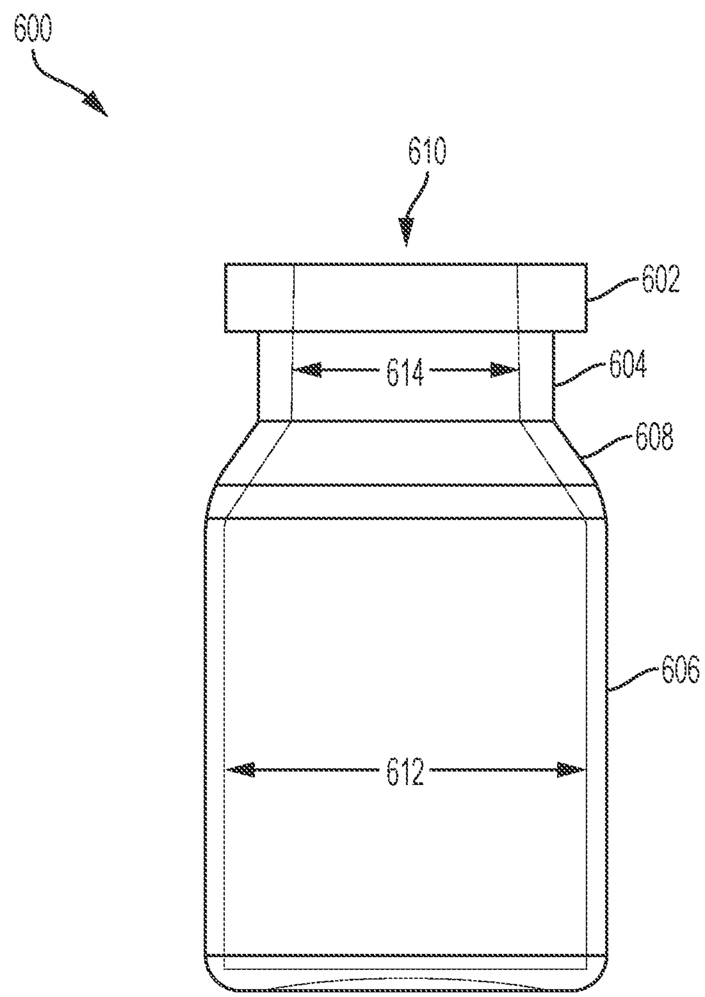
FIG. 6 illustrates an exemplary drug vial.

FIG. 6 illustrates a drug vial 600. The drug vial 600 can be a vial standardized by the International Organization for Standardization (ISO). The drug vial 600 can store or hold any type of liquid drug. As shown in FIG. 6, the drug vial 600 can include a top 602, a neck 604, a main storage area 606, and a transition region 608. A liquid drug can be stored or contained within the drug vial 600 and can generally occupy space within the neck 604, the transition region 608, and/or the main storage area 606 when the drug vial 600 is maintained upright. Typically, a port or opening 610 within the top 602 is used to access the stored liquid drug.

Often, a syringe can be used to extract a liquid drug stored in the drug vial 600. However, for use in a wearable drug delivery device, a syringe is not a practical system for accessing the stored liquid drug. Accordingly, many drug delivery systems that use vials employ pump systems for pumping a stored liquid drug out of the port 610. These pump systems are costly to implement and take up large amounts of space in drug delivery systems intended to be small and compact.

Plunger systems are generally not used to expel a liquid drug from the drug vial 600 due to the varying sizes of the interior diameters of the drug vial 600. As shown in FIG. 6, a diameter 612 of the main storage area 606 is wider than a diameter 614 of the neck 604. The diameter of the neck 604 can also match a width or diameter of the top 602. Further, the diameter or width of the transition region 608 can vary so as to merge the relatively smaller diameter 614 to the relatively larger diameter 612.

The different sizes of the various regions of the drug vial—e.g., between the neck 604 and the main storage area 606—makes the use of a conventional plunger system impractical for expelling a liquid drug from the drug vial 600. For example, a conventional plunger having a width equivalent to the diameter 614 of the neck would be too narrow to be used to expel liquid drug from the larger diameter 612 of the main storage area 606. By contrast, a conventional plunger having a width equivalent to the diameter 612 would be too large to fit through the regions having the narrow diameter 614. There is therefore a need for a system that can efficiently expel a liquid drug from ISO standardized drug vials such as the drug vial 600 that is less costly than conventional pump systems.

Figure 7:
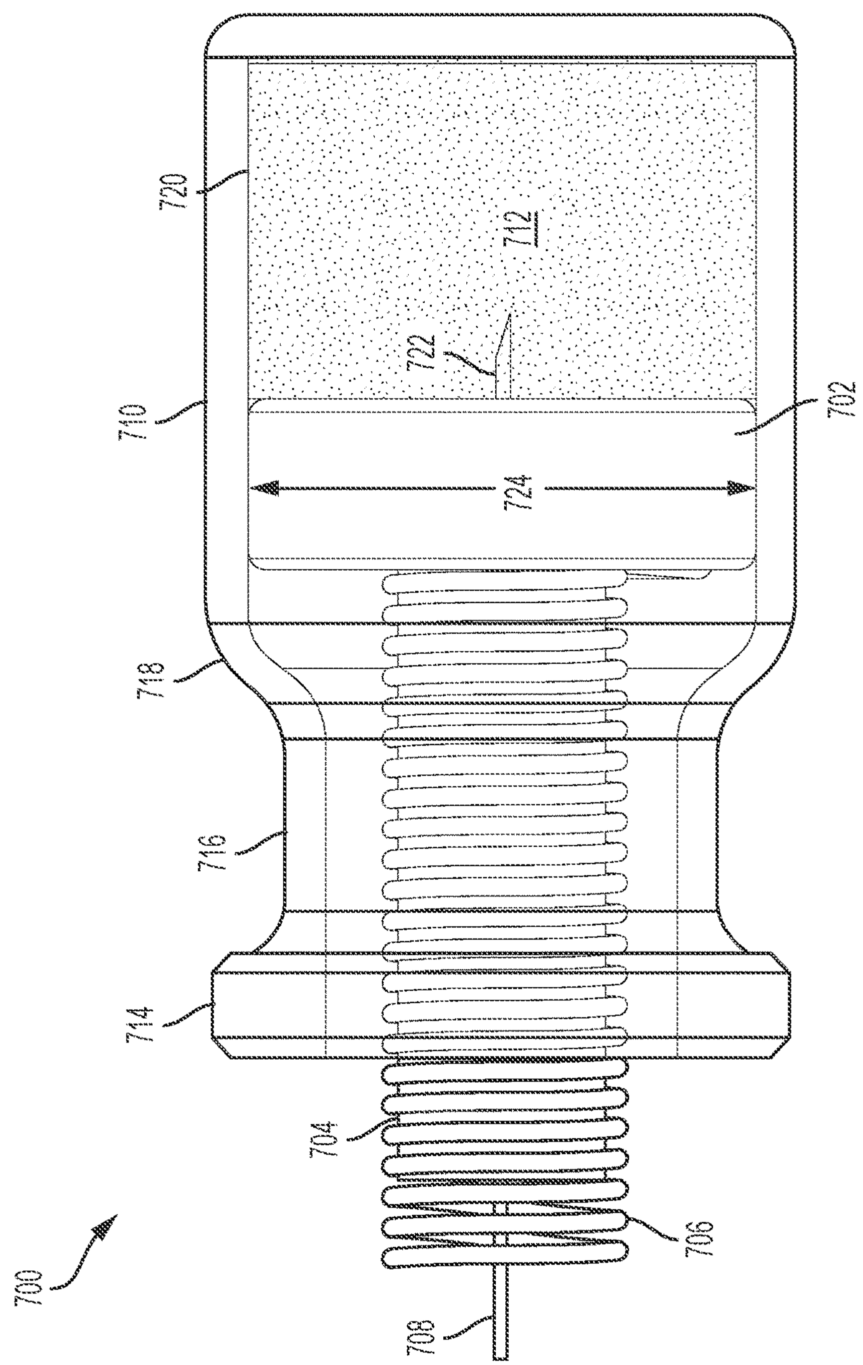
FIG. 7 illustrates an exemplary embodiment of a collapsible plunger system.

FIG. 7 illustrates a collapsible plunger system 700. The collapsible plunger system 700 can be used to expel a liquid drug from a drug vial having internal areas or regions of various sizes and/or widths for holding a liquid drug. As shown in FIG. 7, the collapsible plunger system 700 can include a collapsible plunger 702, a push rod 704, a drive spring 706, and a needle conduit 708. The collapsible plunger 702 can be coupled to the push rod 704. The drive spring 706 can be positioned so that it surrounds at least a portion of the push rod 704. Thus arranged, the drive spring 706 and/or the push rod 704 can provide a force for moving the collapsible plunger 702.

As shown in FIG. 7, the collapsible plunger 702 is positioned inside of a drug vial 710. The drug vial 710 can represent the drug vial 600 of FIG. 6. The drug vial 710 can store or hold a liquid drug 712. Similar to the drug vial 600, the drug vial 710 can include a top 714, a neck 716, a transition region 718, and a main storage area 720. As with the drug vial 600, the diameter or cross-sectional area of the main storage area 720 can be larger than the diameter or cross-sectional area of the neck 716 and the top 714. The collapsible plunger 702 can expand and contract as it is advanced through the drug vial 710 so that it may pass through the various internal diameters of the drug vial 710—e.g., from the top 714, through the neck 716, on to the transition region 718, and then to the main storage area 720.

In various embodiments, the collapsible plunger 702 can be initially positioned outside of the drug vial 710. A drive system (e.g., of a wearable drug delivery system) can be used to advance the collapsible plunger 702 into the drug vial 710 to advance the collapsible plunger 702 further into the drug vial 710. Once inside of the main storage area 720 (e.g., where the liquid drug 712 can be stored), the collapsible plunger 702 can form a seal with the main storage area 720 and can be driven forward further to expel the liquid drug 712 from the drug vial 710.

In various embodiments, the collapsible plunger 702 can be preinstalled into the main storage area 720. For example, the collapsible plunger 702 and the drug vial 710 can be positioned into a wearable drug delivery device substantially as shown in FIG. 7. That is, during manufacturing of a wearable drug delivery device, an operation during manufacture can include installing the collapsible plunger 702 into the main storage area 720, which can already be filled with the liquid drug 712. Once installed in the main storage area 720, the collapsible plunger 702 can be coupled to a drive system that can provide a force to drive the collapsible plunger 702 further into the drug vial 710 when activated after being provided to a user. As such, the collapsible plunger 702 can be provided preinstalled or preloaded into the main storage area 720 when provided to the user as a component of a wearable drug delivery device.

In various embodiments, the collapsible plunger 702 can be deformed or folded and inserted into the neck 714. The deformed collapsible plunger 702 can then be passed through the neck 714 and the adjacent regions 716 and 718, until it reaches the main storage area 720. As the collapsible plunger 702 enters the main storage area 720 from the transition region 718, the collapsible plunger 702 can expand radially to form a seal with the inner surface of the main storage area 720. Once positioned inside of the main storage area 720, the collapsible plunger 702 is ready to be driven forward to expel the liquid drug 712. In various embodiments, the collapsible plunger 702 can be preinstalled into a drug vial 710 that already contains the liquid drug 712 or the drug vial 710 can be empty and can be filled (or refilled) once the collapsible plunger 702 is installed in the main storage area 720. In various embodiments, the collapsible plunger 702 can be formed from a material having a relatively high Poisson's ratio (e.g., a material having a Poisson's ratio close to 0.5).

In operation, as the collapsible plunger 702 advances into the drug vial 710, the liquid drug 712 can be expelled out of the drug vial 710 through the needle conduit 708. The liquid drug 712 can be expelled out of the drug vial 710 through a tip or end 722 of the needle conduit 708. The needle conduit 708 can be positioned through a central portion of the push rod 704. As the push rod 704 and/or the drive spring 706 drives the collapsible plunger 702 into the drug vial 710, the liquid drug 712 can be forced out of the drug vial 710 through the end or tip 722 of the needle conduit 708 and provided to a patient.

To enable the collapsible plunger 702 to be inserted into the vial 700 to assume an operational position, the collapsible plunger 702 can expand and contract as it traverses the various regions of the drug vial 710. In various embodiments, the collapsible plunger 702 can be biased to have a diameter 724 matching a size of the largest region of the drug vial 710 (e.g., the main storage area 720). Accordingly, in a steady state or resting state, the diameter 724 of the collapsible plunger 702 can approximately match a cross-sectional size of the main storage area 720. During insertion of the collapsible plunger 702 into the vial 700, the collapsible plunger 702 traverses a region of the drug vial 700 having a cross-sectional size smaller than the cross-sectional size of the main storage area 720 (e.g., the neck 716). As such, the collapsible plunger 702 can be collapsed to occupy less radial space (e.g., to have a smaller diameter) to pass by the smaller diameter region. Specifically, the collapsible plunger 702 can be compressed radially to a smaller size approximately equal to a cross-sectional size of the smaller region. Once the smaller cross-sectional region is traversed, and the collapsible plunger 702 enters a region having a larger cross-sectional area, the collapsible plunger 702 can expand. For example, as the collapsible plunger 702 enters the main storage area 720 from the neck 716 through the transition region 718, the collapsible plunger 702 can expand such that the diameter of the collapsible plunger 702 is increased. In particular, the collapsible plunger 702 can expand to its biased (steady state) size as indicated by the diameter 724.

By being able to expand and contract, the collapsible plunger 702 can pass through the narrow top 714 and the neck 716 regions of the drug vial 710 to reside in the main storage area 720. Once in the main storage area 720, the collapsible plunger 702 can operate to expel liquid drug 712 from the main storage area 720 out through the needle conduit 708. This enables the collapsible plunger system 700 to be used in a drug delivery system such as, for example, a wearable drug delivery system. Further, the collapsible plunger system 700 allows a standard drug vial—such as the drug vials 600 and 700—to be used as a liquid drug storage container within a wearable drug delivery device that incorporates the collapsible plunger system 700.

The collapsible plunger system 700 can be used with a variety of drug containers and is not limited to an ISO drug vial. In general, the collapsible plunger system 700 can be used to extract a liquid drug from any container, including those having one or more internal regions of different sizes, diameters, and/or cross-sections. Further, the collapsible plunger system 700 can be used with a variety of drive mechanisms and is not limited to being moved by the push rod 704 and/or the drive spring 706. In general, a variety of different mechanical and/or electromechanical drive mechanisms can be used to advance the collapsible plunger 702 from the top 714 of the drug vial 702 to the main storage area 720.

In various embodiments, the diameter 724 of the collapsible plunger 702 can expand and can compress to match the changing diameters of the drug vial 710 as the collapsible plunger traverses regions of the drug vial 710 having different internal diameters and/or cross-sectional areas or sizes. As an example, when the collapsible plunger 702 is positioned within the neck 716, the collapsible plunger 702 can be compressed such that its diameter 724 is smaller than the diameter of the collapsible plunger 702 when the collapsible plunger 702 is positioned within the main storage area 720. By expanding and compressing in size in a radial direction, the collapsible plunger 702 can be used to expel a liquid drug from the drug vial 710 that has various internal liquid drug storage areas of various diameters and/or sizes.

The collapsible plunger 702 can comprise a plastic, rubber, and/or an elastomer material. The collapsible plunger system 700 can be operated to start and stop forward movement of the collapsible plunger 702 as desired to expel the liquid drug over multiple doses. Alternatively, the collapsible plunger system 700 can be operated to provide the liquid drug to the user over a single dose.

Figure 8:
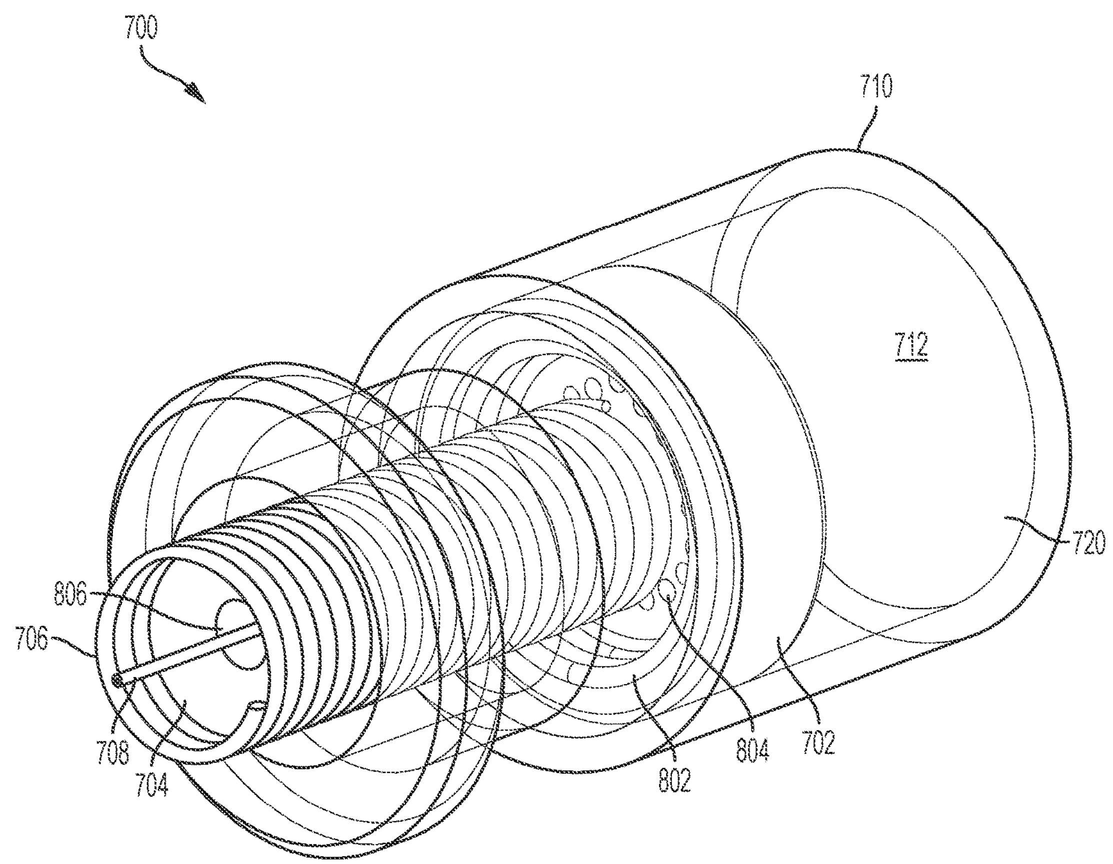
FIG. 8 illustrates a second view of the collapsible plunger system of FIG. 7.
Figure 9:
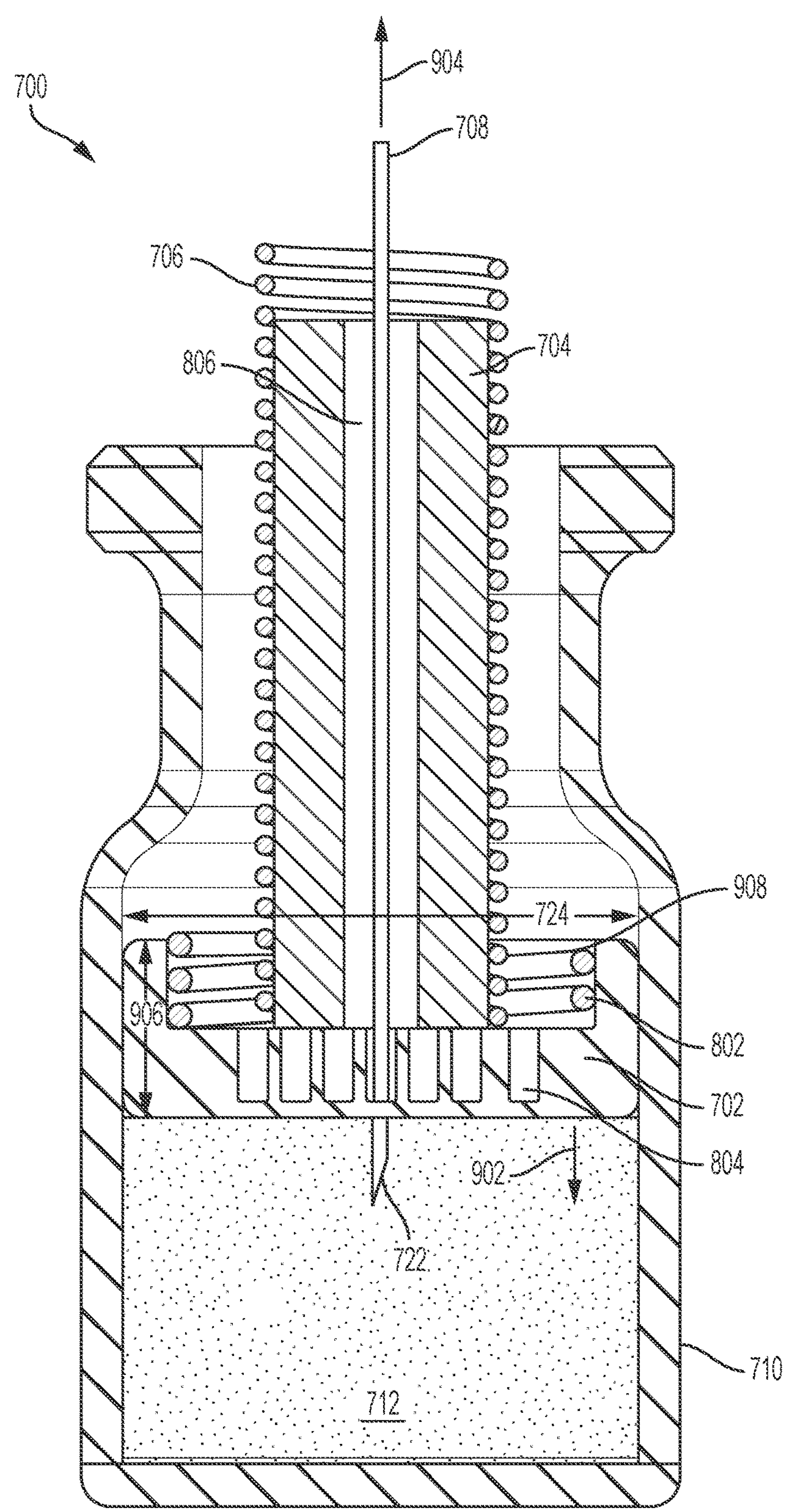
FIG. 9 illustrates a cross-sectional view of the collapsible plunger system of FIG. 7.

FIG. 8 illustrates a second view of the collapsible plunger system 700. The top 714, the neck 716, and the transition region 718 are shown in phantom to reveal more detail of the collapsible plunger system 700. As shown in FIG. 8, an internal portion of the collapsible plunger 702 includes an opening or cavity 908 (as shown in FIG. 9). A radial torsion spring 802 can be positioned inside of the interior region of the collapsible plunger 702. The radial torsion spring 802 can apply a radial outward force to expand the collapsible plunger 702 radially outward from a compressed state to an expanded state. The radial torsion spring 802 can accordingly operate to provide a steady state or resting diameter of the collapsible plunger 702. In various embodiments, other springs can be used in lieu of the radial torsion spring 802. For example, other springs such as a spring clip could be used. Accordingly, the collapsible plunger system 700 is not limited to use of the radial torsion spring 802.

As further shown in FIG. 8, the collapsible plunger 702 can include coring areas 804. The coring areas 804 can aid compression of the collapsible plunger 702. The coring areas 804 can be open areas within the collapsible plunger 702 where material for forming the collapsible plunger 702 is removed or not provided. As will be appreciated, the cavity and the coring areas 804 can result in the collapsible plunger 702 having enhanced flexibility or compressibility, making it easier to compress the collapsible plunger 702 when inserting it into the vial 710. The push rod 704 is also shown to include an opening 806 that can accommodate the needle conduit 708. The opening 806 can extend through the push rod 704 to enable the end 722 of the needle conduit 708 to extend through the push rod 704 and beyond the collapsible plunger 702.

FIG. 9 illustrates a cross-sectional side view of the plunger system 700. Indicator 902 illustrates a direction of the plunger 702 when advanced into the drug container 710. Indicator 904 illustrates a direction of the flow of the liquid drug 712 out of the drug container 710 through the needle conduit 708. As further shown in FIG. 9, the central opening 806 within the push rod 704 provides a pathway for the needle conduit 708 to reach into the drug container 710.

FIG. 9 further illustrates an exemplary design of the collapsible plunger. As shown in FIG. 9, and discussed above, the plunger 702 has an outer diameter 724 (e.g., a horizontal diameter relative to the orientation of the drug container 710 as depicted in FIG. 9). As discussed above, the outer diameter 724 can be adjusted and can be changed based on the position of the plunger 702 within the drug container 710. The plunger 702 can also have a thickness or width 906 (e.g., a vertical thickness relative to the orientation of the drug container 710 as depicted in FIG. 9).

A portion of the plunger 702 can include an open area 908. The open area 908 can have a diameter that is less than the outer diameter 724 of the plunger 702 and may also extend along only a portion of the thickness 906. In various embodiments, the open area 908 can extend approximately halfway through the plunger 702 relative to the thickness 906. The open area 908 can be centered within the collapsible plunger 702. The torsion spring 802 can be positioned within the open area 802. The open area 908 can be considered to be a cavity or opening of the plunger 702.

FIG. 9 further shows the positioning of the coring areas 804 relative to the open area 802. The coring areas 804 can be provided from the open area 802 into a portion of the remaining thickness 906 of the plunger 702. The coring areas 804 can be open space areas that are, for example, drilled or formed into the plunger 702. The surface of the collapsible plunger 702 that is in contact with the liquid drug 712 can be considered a front surface of the collapsible plunger 702. The surface of the collapsible plunger 702 positioned closer to the top 714 of the drug vial 710 can be considered a back surface of the collapsible plunger 702. The front surface can be substantially flat or planar. The back surface can surround the open area 908. The side of the collapsible plunger 702 that joins the front and back surfaces can form a seal with the main storage area 720 of the drug vial 710.

Figure 10:
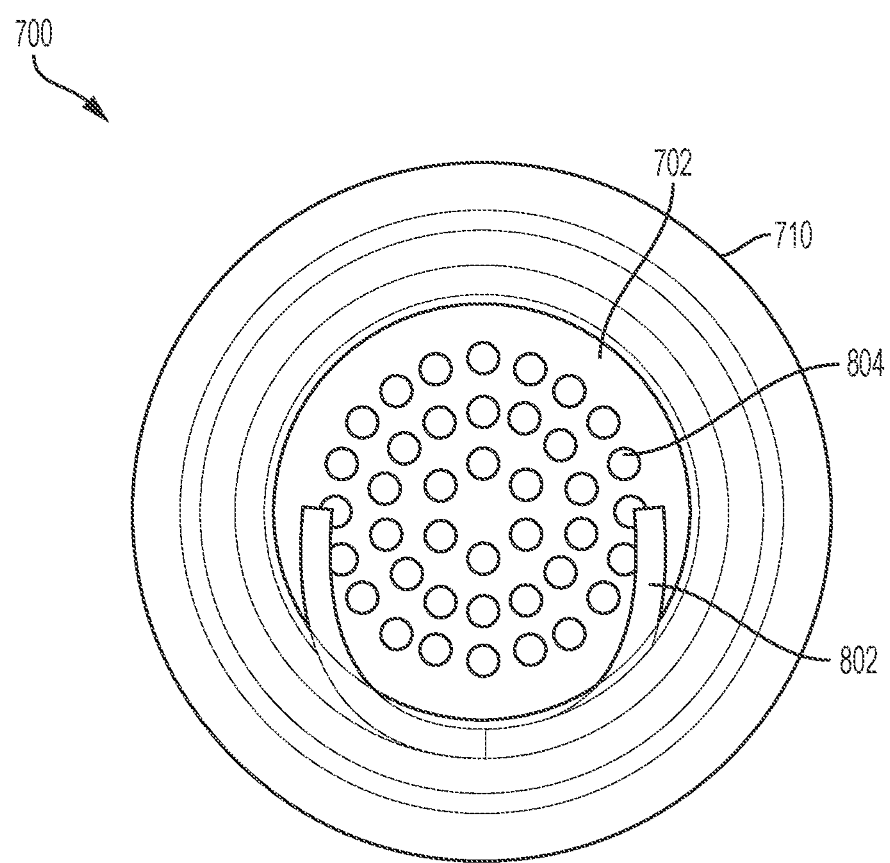
FIG. 10 illustrates a third view of the collapsible plunger system of FIG. 7.

FIG. 10 illustrates a head on view of the collapsible plunger system 700. In particular, FIG. 10 illustrates a view through the top 712 of the drug vial 710 relative to the depiction of the collapsible plunger system 700 in FIGS. 7-9 such that the collapsible plunger 702 is within the main storage area 720.

As shown in FIG. 10, the torsion spring 802 is wound to allow collapse of the outer diameter of the collapsible plunger 702, to enable the plunger 702 to fit through various regions of the drug vial 710. The torsion spring 802 can apply a radial outward force. For example, when the collapsible plunger 702 moves from a region having a relatively smaller diameter (e.g., the neck 716) to a region having a relatively larger diameter (e.g., the main storage area 720), the torsion spring 802 can cause the collapsible plunger 702 to expand radially. The radial force provided by the torsion spring 802 can provide a seal between the outer portion of the collapsible plunger 702 and the internal walls or surface of the drug vial 710.

Figure 11:
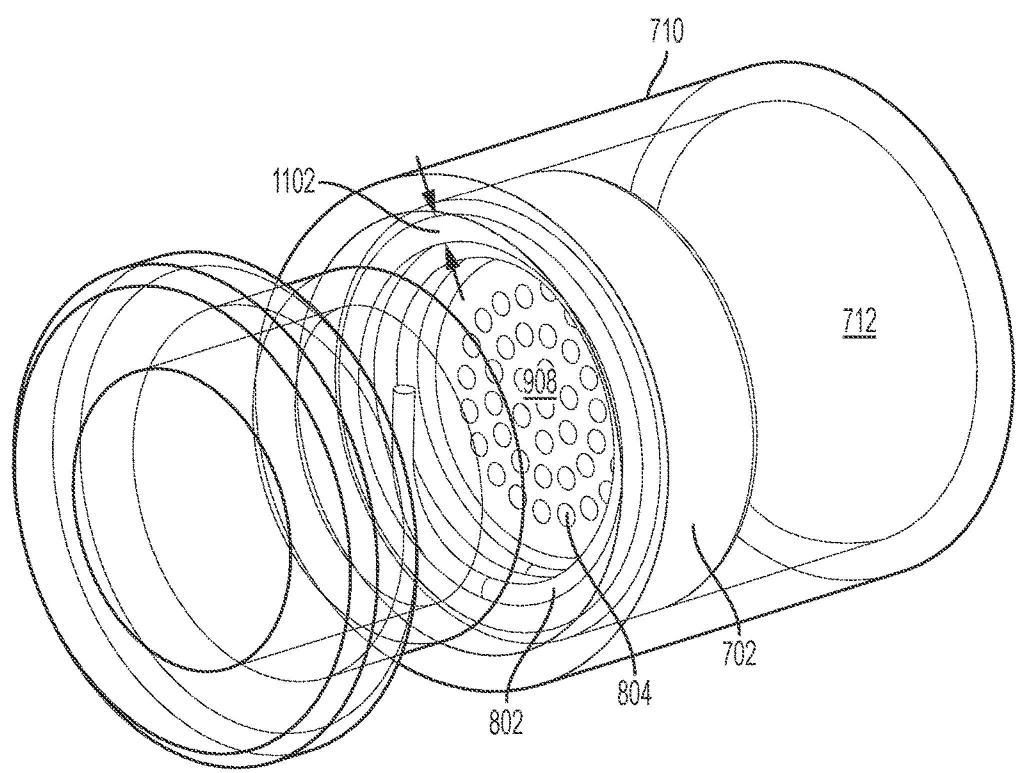
FIG. 11 illustrates a fourth view of the collapsible plunger system of FIG. 7.

FIG. 11 illustrates a further view of the collapsible plunger system 700. Portions of the drug vial 710 are shown in phantom in FIG. 11 to reveal more detail of the collapsible plunger system 700. As shown in FIG. 11, the selective coring areas 804 can aid radial compression of the collapsible plunger. Further, a thickness 1102 of the outer wall of the collapsible plunger 702 can be tuned to result in a desired degree of radial compression. That is, the size of the open area or cavity 908 can be wider or smaller to adjust the thickness 1102 of the outer wall of the collapsible plunger 702 that surrounds the cavity 908. In general, as the thickness 1102 is decreased, the collapsible plunger 702 can be radially compressed by a larger amount and/or the amount of force required to collapse the collapsible plunger 702 can be smaller. The thickness 1102 can be a difference between the diameter 724 and the diameter of the open area 908 when, for example, when the collapsible plunger 702 is expanded to its maximum size radially.

Figure 12:
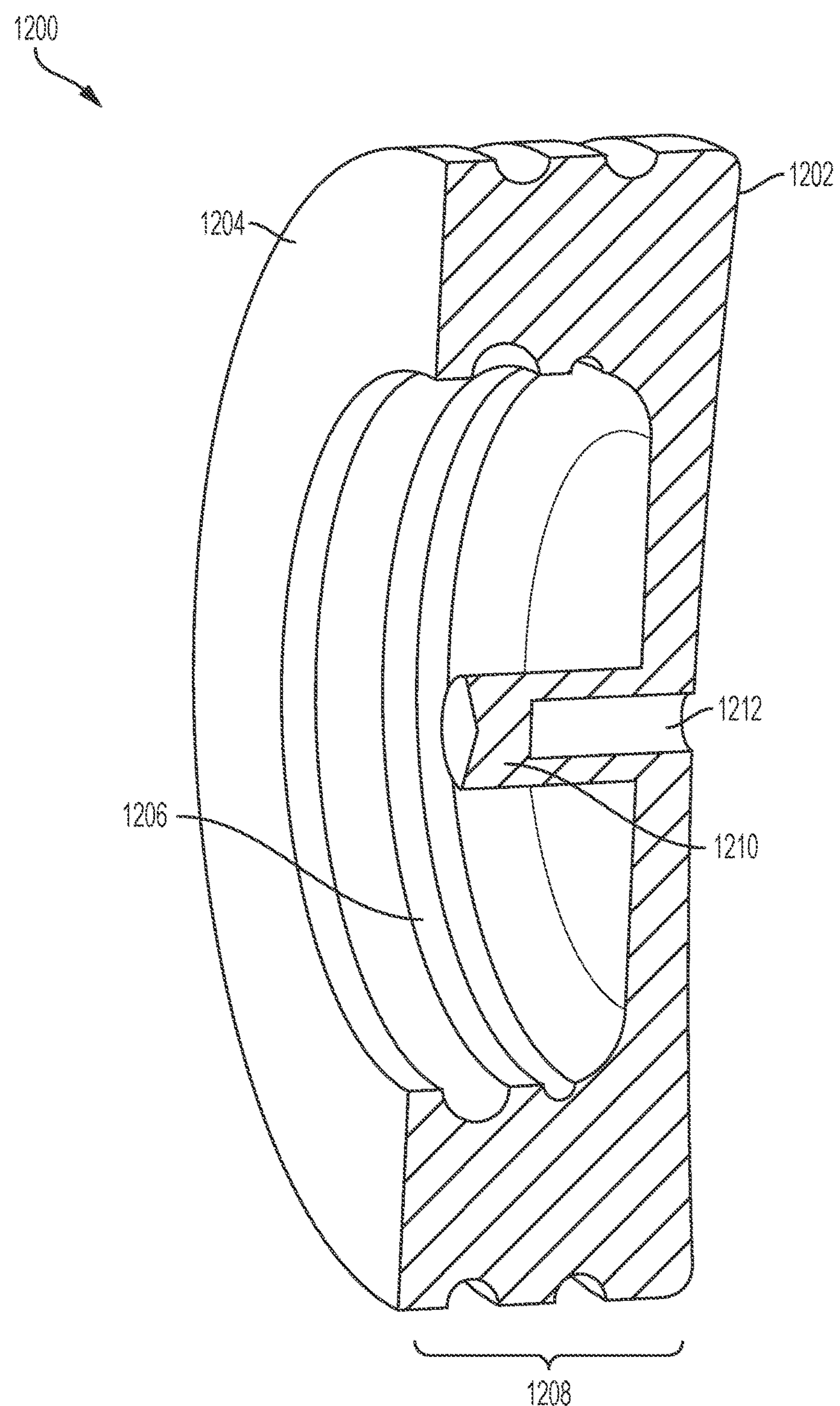
FIG. 12 illustrates an exemplary embodiment of a collapsible plunger.

FIG. 12 illustrates a cross-section of a second collapsible plunger 1200. The collapsible plunger 1200 can function similarly to the collapsible plunger 702. The collapsible plunger 1200 can be used in place of the collapsible plunger 702 in the collapsible plunger system 700.

As shown in FIG. 12, the collapsible plunger 1200 can include a front face or surface 1202 and a back face or surface 1204. The collapsible plunger 1200 can be positioned in a drug vial such that the front surface 1202 is positioned further into the drug vial relative to the back surface 1204 (i.e., so that the liquid drug contacts the front surface 1202).

The collapsible plunger 1200 can include an opening or cavity 1206. The opening 1206 can have a circular shape and can be centered about the collapsible plunger 1200. The back surface 1204 can surround the opening 1206. The opening 1206 can extend into a portion of a total thickness or width 1208 of the collapsible plunger 1200. Specifically, the opening 1206 can extend into a portion of the collapsible plunger 1200 without passing entirely through the collapsible plunger.

A torsion spring (not shown in FIG. 12 for simplicity) can be positioned within the opening 1206. The opening 1206 can be shaped to hold and/or support any embedded torsion spring positioned within the opening 1206. In various embodiments, the collapsible plunger 1200 can be used without an embedded torsion spring. In various embodiments, a push rod can be positioned in the opening 1206 and can have a diameter matching a diameter of a neck of a vial. The push rod positioned in the opening 1206 can provide a radial outward force and can aid the formation of a seal by the outer surfaces of the collapsible plunger 1200. The push rod can further prevent unwanted compression by the collapsible plunger 1200 when the collapsible plunger 1200 is positioned in an area of a vial having a diameter larger than the neck of the vial.

The collapsible plunger 1200 can further include a stem 1210. The stem 1210 can extend from the front surface 1202 through the opening 1206 toward the back surface 1204. The stem 1210 can be cylindrical in shape and can have a circular cross-section. The stem 1210 can be positioned at a center of the collapsible plunger 1200. The stem 1210 can include an open area or pocket 1212. The stem 1210 can be used as a guide for a needle conduit (such as the needle conduit 708 of FIG. 7) and the pocket 1212 can provide an area for a tip (such as the tip 722 of FIG. 7) of the needle conduit. Specifically, a needle conduit can be guided and supported by the stem 1210 and can include a needle tip positioned within the pocket 1212 such that the tip of the needle conduit does not extend beyond the front surface 1202.

FIG. 12 illustrates the collapsible plunger 1200 in an expanded state and/or a steady state position. The collapsible plunger 1200 can be radially compressed from the expanded state shown in FIG. 12 to pass through areas of a drug vial having reduced diameters and/or cross-sections as described above.

Figure 13:
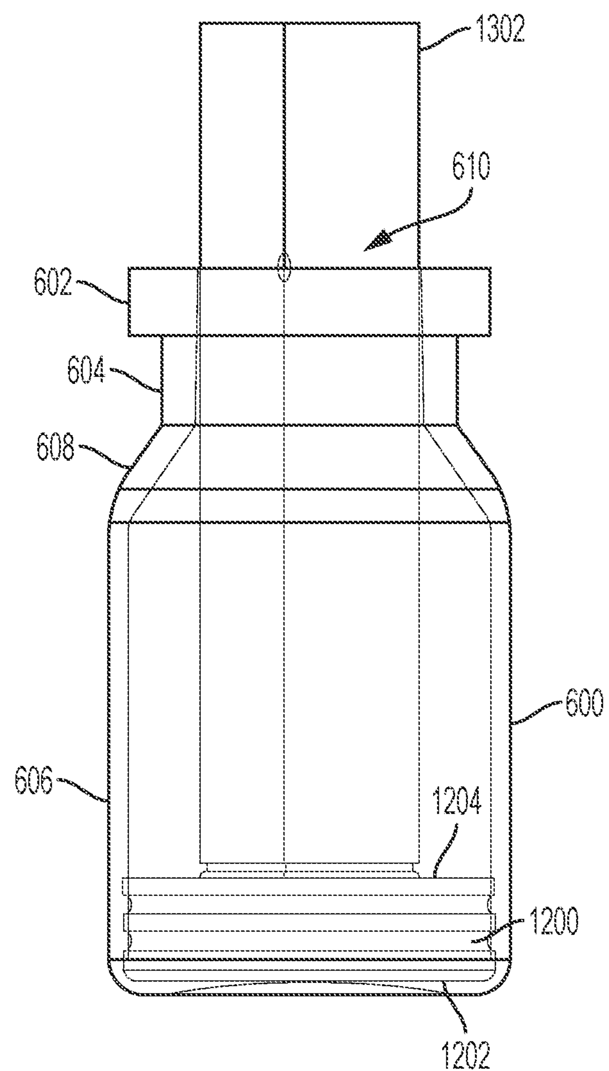
FIG. 13 illustrates an exemplary use of the collapsible plunger of FIG. 12.

FIG. 13 illustrates the collapsible plunger 1200 positioned within the drug vial 600. As shown in the FIG. 13, the collapsible plunger 1200 is positioned within the main storage area 606 of the drug vial 600. The collapsible plunger 1200 can be coupled to a push rod 1302. The push rod 1302 can be coupled to a back surface 1204 of the collapsible plunger 1200 and/or to an internal portion of the collapsible plunger 1200 (e.g., within the opening 1206). The stem 1210 and the pocket 1212 allow a tip of a needle conduit to be positioned adjacent to the front surface 1202 without extending beyond the front surface 1202. Accordingly, the front surface 1202 can be pressed against a bottom surface of the drug vial 600 as shown without damaging the needle tip against the bottom surface. The push rod 1302 can include a port or opening to enable liquid drug held in the vial 600 to be expelled through the collapsible plunger 1200 and a needle conduit positioned in the push rod 1302.

As shown in FIG. 13, the push rod 1302 can have a diameter approximately matching an inner diameter of the neck region 604. The push rod 1302 can provide a radial outward force on the collapsible plunger 1200 to ensure the collapsible plunger 1200 forms a seal with the internal surface of the main storage area 606.

As with the collapsible plunger 702, the collapsible plunger 1200 can be provided as part of a wearable drug delivery device and can be preinstalled in the main storage area 606. In various embodiments, when provided to a user, the collapsible plunger 1200 can be positioned with the main storage area 606 and can be adjacent to the transition region 608. The main storage area 606 can be prefilled with a liquid drug. Accordingly, when provided to the user, the collapsible plunger 1200 can be ready for use—that is, the collapsible plunger 1200 can form a seal with the main storage area 606 and can be driven forward to expel a stored liquid drug from the main storage area 606 during operation of the wearable drug delivery device in which the collapsible plunger 1200 can be used.

Figure 14:
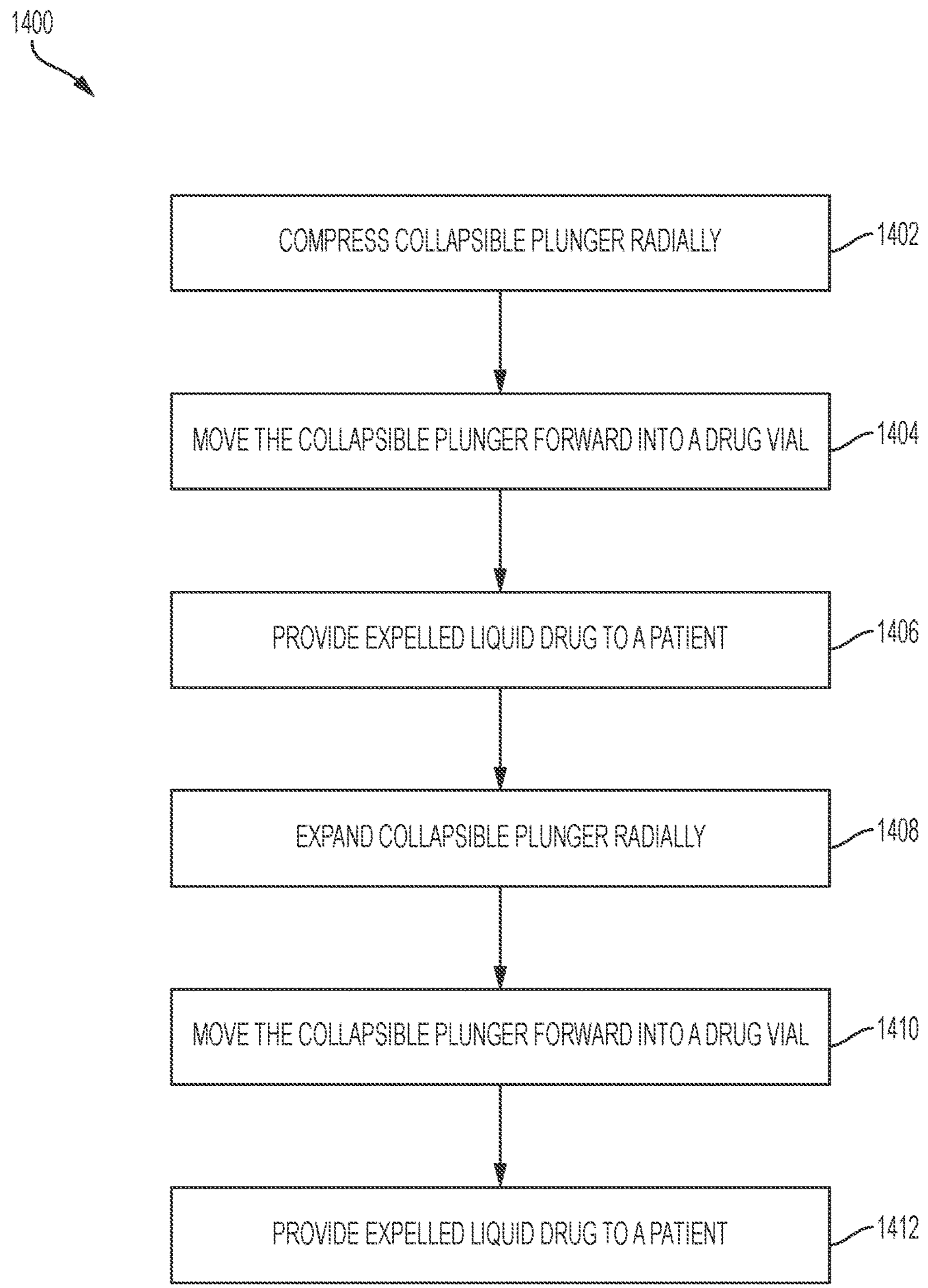
FIG. 14 illustrates an exemplary method of operation for the collapsible plunger system of FIGS. 7-11 and/or the collapsible plunger of FIGS. 12 and 13.

FIG. 14 illustrates an exemplary method of operation 1400 for a collapsible plunger system. The method of operation 1400 can be implemented by the plunger system 700 using the collapsible plunger 702 or the collapsible plunger 1200 or the plunger system depicted in FIG. 13.

At 1402, a collapsible plunger can be compressed radially. A diameter of the collapsible plunger can be reduced. As an example, the diameter of the collapsible plunger can be reduced from a larger first diameter to a smaller second diameter. The larger first diameter can be a diameter of the collapsible plunger in an uncompressed state and/or a steady state of operation. The collapsible plunger can be compressed radially at 1402 to enter a region of a drug vial having a diameter than is smaller than the first diameter of the collapsible plunger. Compressing of the collapsible plunger can occur as the collapsible plunger is forced into a region of a smaller diameter.

At 1404, the collapsible plunger can be moved or advanced forward into the drug vial. The collapsible plunger can be moved forward through the region of the drug vial having a diameter smaller than the first diameter of the collapsible plunger. The diameter of the collapsible plunger can be reduced at 1402 to a diameter (e.g., the second diameter) approximately matching the region of drug vial. As the collapsible plunger is moved forward, an amount of liquid drug can be expelled from the drug vial. As an example, the liquid drug can be expelled through a needle conduit positioned in and/or through the collapsible plunger. In various embodiments, as the collapsible plunger is moved forward no liquid drug can be expelled until the collapsible plunger is positioned within and moved forward within a main storage area of a drug vial.

At 1406, the expelled liquid drug can be provided to a patient. The expelled liquid drug can be provided to the patient via the needle conduit and/or a fluid delivery system or path coupled to the needle conduit.

At 1408, the collapsible plunger can be expanded radially. A diameter of the collapsible plunger can be increased. As an example, the diameter of the collapsible plunger can be increased from the smaller second diameter to the larger first diameter. The collapsible plunger can be expanded radially at 1408 to enter a region of the drug vial having a diameter that is larger than the second diameter of the collapsible plunger.

At 1410, the collapsible plunger can be moved or advanced forward into the drug vial. The collapsible plunger can be moved forward through the region of the drug vial having a diameter larger than the second diameter of the collapsible plunger. The diameter of the collapsible plunger can be increased at 1408 to a diameter (e.g., the first diameter) approximately matching the region of drug vial. As the collapsible plunger is moved forward, an amount of liquid drug can be expelled from the drug vial.

At 1412, the expelled liquid drug can be provided to a patient. The expelled liquid drug can be provided to the patient via the needle conduit and/or a fluid delivery system or path coupled to the needle conduit.

As will be understood by a person of ordinary skill in the art, the method of operation 1400 can be modified to provide any order of compression and/or expansion of a collapsible plunger to traverse one or more regions of a drug vial having one or more different diameters or sizes. As an example, the method of operation 1400 can be implemented in an order to enable the collapsible plunger to first expand from a compressed state and then to be compressed from the expanded state as it traverses various different regions of a drug vial. Further, compression, expansion, and/or forward movement of the collapsible plunger can be paused or stopped as necessary to enable the collapsible plunger system to provide multiple doses of a liquid drug to a patient. Alternatively, the collapsible plunger system can be operated to continuously traverse a drug vial to provide the stored liquid drug to the user in a single dose. Further, advancement of the collapsible plunger forward can apply a force relative to the internal walls of a drug vial to compress the collapsible plunger. The method of operation 1400 can also be modified as will be appreciated by a person of ordinary skill in the art to be installed into a main storage area or largest diameter area of a drug vial, and to expel a liquid drug thereafter.

The plunger system 100, the plunger system 300, and/or the plunger system 400 can be combined or can be part of the collapsible plunger system 700 or can be used with the collapsible plunger 702 or the collapsible plunger 1200. For example, the collapsible plunger system 700, the collapsible plunger 702, or the collapsible plunger 1200 can be combined with the plunger system 100, the plunger system 300, and/or the plunger system 400 to enable the collapsible plungers 702 and 1200 to be rotated to overcome a static friction as described herein. Accordingly, the method of operation 1400 can include an operation of rotating a collapsible plunger to overcome a static friction prior to moving the collapsible plunger forward into a drug container.

The embodiments described herein provide numerous benefits over conventional systems. As will be appreciated by a person of ordinary skill in the art, vials are one of the most common primary containers for holding pharmaceutical drugs. Most delivery mechanisms that are used with vials can only pull a stored liquid out of the vial using a vacuum. These vacuums are typically limited to atmospheric pressure (e.g., −14.7 psi (29.9 inHg)). The embodiments described herein—in particular, the collapsible plunger system 700, the collapsible plunger 702, and/or the collapsible plunger 1200—provide for significantly higher pressure capability. As a result of this increase pressure capability, more of the drug from the vial can be removed (i.e., most of the drug stored in the drug container can be removed with little to no hold up volume). The embodiments described herein therefore provide significant benefits to the pharmaceutical industry since standard filling processes can be used for vials, costs can be kept low, and overfilling containers to account for hold up volume can be reduced since the embodiments described herein can significantly reduce hold up volume.

The following examples pertain to further embodiments:

Example 1 is a system comprising a drug container configured to hold a liquid drug, a plunger disposed within the drug container, a rotation system configured to rotate the plunger about a central axis of the plunger, and a drive system configured to move the plunger along the central axis within the drug container to expel a portion of the liquid drug from the drug container for delivery to a patient.

Example 2 is an extension of Example 1 or any other example disclosed herein, wherein the rotation system is configured to rotate the plunger by a predetermined amount to overcome a static friction between the plunger and the drug container.

Example 3 is an extension of Example 2 or any other example disclosed herein, wherein the rotation system is configured to rotate the plunger in a clockwise direction.

Example 4 is an extension of Example 2 or any other example disclosed herein, wherein the rotation system is configured to rotate the plunger in a counterclockwise direction.

Example 5 is an extension of Example 2 or any other example disclosed herein, wherein the rotation system is configured to rotate the plunger prior to the drive system moving the plunger along the central axis of the drug container.

Example 6 is an extension of Example 1 or any other example disclosed herein, wherein the drug container has a circular cross-section.

Example 7 is an extension of Example 1 or any other example disclosed herein, wherein the plunger comprises an elastomer.

Example 8 is an extension of Example 1 or any other example disclosed herein, wherein the drive system is configured to expel the portion of the liquid drug through a port of the drug container by moving the plunger towards the port.

Example 9 is an extension of Example 1 or any other example disclosed herein, wherein the drive system is configured to expel the portion of the liquid drug through a port of the plunger by moving the plunger within the drug container.

Example 10 is an extension of Example 1 or any other example disclosed herein, wherein the drive system comprises an electromechanical system.

Example 11 is an extension of Example 1 or any other example disclosed herein, wherein the drive system comprises a push rod coupled to the plunger.

Example 12 is an extension of Example 1 or any other example disclosed herein, wherein the drive system comprises a drive spring.

Example 13 is an extension of Example 1 or any other example disclosed herein, wherein the rotation system comprises an electromechanical system.

Example 14 is an extension of Example 1 or any other example disclosed herein, wherein the rotation system comprises a push rod coupled to the plunger.

Example 15 is an extension of Example 14 or any other example disclosed herein, wherein the rotation system is configured to rotate the plunger by rotating the push rod.

Example 16 is an extension of Example 1 or any other example disclosed herein, wherein the rotation system comprises a torsion spring.

Example 17 is an extension of Example 1 or any other example disclosed herein, wherein the drug container is a vial standardized by the International Organization for Standardization (ISO).

Example 18 is an extension of Example 1 or any other example disclosed herein, wherein the drug container is a drug cartridge.

Example 19 is an extension of Example 1 or any other example disclosed herein, wherein the system is a part of a wearable drug delivery system.

Example 20 is a method for expelling a liquid drug from a drug container, comprising positioning a plunger inside of a drug container, rotating the plunger about a central axis of the plunger, moving the plunger along the central axis of the drug container to expel the liquid drug from the drug container, and delivering the expelled liquid drug to a patient.

Example 21 is an extension of Example 20 or any other example disclosed herein, wherein rotating comprises rotating the plunger by a predetermined amount to overcome a static friction between the plunger and the drug container.

Example 22 is an extension of Example 21 or any other example disclosed herein, further comprising rotating the plunger in a clockwise direction.

Example 23 is an extension of Example 21 or any other example disclosed herein, further comprising rotating the plunger in a counterclockwise direction.

Example 24 is an extension of Example 21 or any other example disclosed herein, further comprising rotating the plunger prior to moving the plunger along the central axis.

Example 25 is an extension of Example 20 or any other example disclosed herein, further comprising expelling the liquid drug through a port of the drug container.

Example 26 is an extension of Example 20 or any other example disclosed herein, further comprising expelling the liquid drug through a port of the plunger.

The following examples pertain to additional further embodiments:

Example 1 is a plunger system comprising a collapsible plunger, a push rod coupled to the plunger, a drive spring positioned around the push rod, and a needle conduit positioned through the push rod.

Example 2 is an extension of Example 1 or any other example disclosed herein, the collapsible plunger comprising a front surface, a back surface, and a cavity extending into the plunger and surrounded by the back surface, wherein the cavity forms an internal portion of the collapsible plunger.

Example 3 is an extension of Example 2 or any other example disclosed herein, wherein the cavity is circular shaped and centered about a central axis of the collapsible plunger.

Example 4 is an extension of Example 2 or any other example disclosed herein, further comprising a radial torsion spring positioned in the cavity of the collapsible plunger.

Example 5 is an extension of Example 4 or any other example disclosed herein, wherein the radial torsion spring is configured to provide an outward radial force on the collapsible plunger.

Example 6 is an extension of Example 5 or any other example disclosed herein, wherein the radial torsion spring is configured to maintain a predetermined diameter of the collapsible plunger.

Example 7 is an extension of Example 2 or any other example disclosed herein, wherein the collapsible plunger comprises coring areas extending from the cavity of the collapsible plunger toward the front surface of the collapsible plunger.

Example 8 is an extension of Example 2 or any other example disclosed herein, wherein an end of the push rod and an end of the drive spring are positioned within the cavity of the collapsible plunger.

Example 9 is an extension of Example 2 or any other example disclosed herein, wherein the cavity extends approximately halfway along a thickness of the collapsible plunger.

Example 10 is an extension of Example 1 or any other example disclosed herein, wherein the push rod comprises an opening extending through the push rod, wherein the needle conduit is positioned within the opening of the push rod.

Example 11 is an extension of Example 10 or any other example disclosed herein, wherein the needle conduit comprises a tip extending beyond the front surface of the plunger.

Example 12 is an extension of Example 1 or any other example disclosed herein, wherein at least one of the drive spring and the push rod are configured to apply a force to the collapsible plunger to move the collapsible plunger.

Example 13 is an extension of Example 1 or any other example disclosed herein, wherein the collapsible plunger comprises an elastomer.

Example 14 is an extension of Example 1 or any other example disclosed herein, wherein the collapsible plunger comprises a stem extending from the front surface into the cavity and toward the back surface of the collapsible plunger.

Example 15 is an extension of Example 14 or any other example disclosed herein, wherein the stem is centered about a central axis of the collapsible plunger.

Example 16 is an extension of Example 15 or any other example disclosed herein, wherein the stem comprises a pocket.

Example 17 is an extension of Example 16 or any other example disclosed herein, wherein the pocket comprises an open area configured to retain an end of the needle conduit.

Example 18 is an extension of Example 1 or any other example disclosed herein, wherein the collapsible plunger is configured to compress radially.

Example 19 is an extension of Example 1 or any other example disclosed herein, wherein the plunger system comprises a part of a wearable drug delivery device.

Example 20 is a method comprising compressing a collapsible plunger radially, wherein a diameter of the collapsible plunger is reduced from a first diameter to a second diameter, wherein the first diameter is larger than the second diameter and moving the collapsible plunger forward through a first portion of a drug container having a diameter approximately matching the second diameter of the collapsible plunger.

Example 21 is an extension of Example 20 or any other example disclosed herein, further comprising expelling a liquid drug from the drug container as the collapsible plunger is moving forward.

Example 22 is an extension of Example 21 or any other example disclosed herein, further comprising providing the expelled liquid drug to a patient.

Example 23 is an extension of Example 21 or any other example disclosed herein, further comprising expanding the collapsible plunger radially, wherein the diameter of the collapsible plunger is increased to the first diameter and moving the collapsible plunger forward through a second portion of the drug container having a diameter approximately matching the first diameter of the collapsible plunger.

Example 24 is an extension of Example 23 or any other example disclosed herein, wherein expanding comprises applying a radial outward force on the collapsible plunger by an internal radial torsion spring positioned within the collapsible plunger.

Example 25 is an extension of Example 23 or any other example disclosed herein, wherein moving the collapsible plunger forward comprises applying a force on the collapsible plunger to advance the collapsible plunger into the drug container.

Example 26 is an extension of Example 21 or any other example disclosed herein, further comprising positioning a needle into the collapsible plunger to provide a fluid path for the expelled liquid drug.

Example 27 is an extension of Example 26 or any other example disclosed herein, further comprising extending the end of the needle beyond the collapsible plunger into the drug container.

Example 28 is an extension of Example 26 or any other example disclosed herein, further comprising providing a pocket within the collapsible plunger to retain the end of a needle.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A plunger system, comprising:

a collapsible plunger;

a push rod coupled to the plunger;

a drive spring positioned around the push rod; and a needle conduit positioned through the push rod, the collapsible plunger comprising a front surface, a back surface, and a cavity extending into the plunger and surrounded by the back surface, wherein the cavity forms an internal portion of the collapsible plunger, wherein a radial torsion spring is positioned in the cavity of the collapsible plunger.

2. The plunger system of claim 1, wherein the cavity is circular shaped and centered about a central axis of the collapsible plunger.

3. The plunger system of claim 1, wherein the collapsible plunger comprises coring areas extending from the cavity of the collapsible plunger toward the front surface of the collapsible plunger.

4. The plunger system of claim 1, wherein an end of the push rod and an end of the drive spring are positioned within the cavity of the collapsible plunger.

5. The plunger system of claim 1, wherein the cavity extends approximately halfway along a thickness of the collapsible plunger.

6. The plunger system of claim 1, wherein at least one of the drive spring and the push rod are configured to apply a force to the collapsible plunger to move the collapsible plunger.

7. The plunger system of claim 1, wherein the collapsible plunger comprises an elastomer.

8. The plunger system of claim 1, wherein the collapsible plunger is configured to compress radially.

9. The plunger system of claim 1, wherein the plunger system comprises a part of a wearable drug delivery device.

10. The plunger system of claim 1, wherein the push rod comprises an opening extending through the push rod, wherein the needle conduit is positioned within the opening of the push rod.

11. The plunger system of claim 10, wherein the needle conduit comprises a tip extending beyond the front surface of the plunger.

12. The plunger system of claim 1, wherein the radial torsion spring is configured to provide an outward radial force on the collapsible plunger.

13. The plunger system of claim 12, wherein the radial torsion spring is configured to maintain a predetermined diameter of the collapsible plunger.

14. The plunger system of claim 1, wherein the collapsible plunger comprises a stem extending from the front surface into the cavity and toward the back surface of the collapsible plunger.

15. The plunger system of claim 14, wherein the stem is centered about a central axis of the collapsible plunger.

16. The plunger system of claim 15, wherein the stem comprises a pocket.

17. The plunger system of claim 16, wherein the pocket comprises an open area configured to retain an end of the needle conduit.

18. A plunger system, comprising:

a collapsible plunger;

a push rod coupled to the plunger;

a drive spring positioned around the push rod;

a needle conduit positioned through the push rod; and a rotation system configured to rotate the plunger about a central axis of the plunger, wherein the rotation system is configured to rotate the plunger by a predetermined amount to overcome a static friction between the plunger and a drug container in which the plunger is disposed.

19. The plunger system of claim 18, wherein the rotation system comprises a torsion spring.

20. The plunger system of claim 18, wherein the drug container is a vial standardized by the International Organization for Standardization (ISO).

21. The plunger system of claim 18, wherein the rotation system is configured to rotate the plunger prior to the plunger being moved along the central axis of the drug container.

22. The plunger system of claim 21, wherein the rotation system is configured to rotate the plunger by rotating the push rod.

* * * * *